(12) United States Patent
Bulard

(10) Patent No.: US 11,224,498 B2
(45) Date of Patent: Jan. 18, 2022

(54) IMPLANTATION METHOD USING A PIEZOELECTRIC DEVICE

(71) Applicant: Ronald A. Bulard, Ardmore, OK (US)

(72) Inventor: Ronald A. Bulard, Ardmore, OK (US)

( * ) Notice: Subject to any disclaimer, the term of this patent is extended or adjusted under 35 U.S.C. 154(b) by 192 days.

(21) Appl. No.: 16/603,440

(22) PCT Filed: Apr. 5, 2018

(86) PCT No.: PCT/US2018/026172
§ 371 (c)(1),
(2) Date: Oct. 7, 2019

(87) PCT Pub. No.: WO2018/187526
PCT Pub. Date: Oct. 11, 2018

(65) Prior Publication Data
US 2020/0146788 A1    May 14, 2020

Related U.S. Application Data

(60) Provisional application No. 62/481,736, filed on Apr. 5, 2017.

(51) Int. Cl.
*A61C 8/00* (2006.01)
*A61C 1/07* (2006.01)

(52) U.S. Cl.
CPC .............. *A61C 8/0089* (2013.01); *A61C 1/07* (2013.01)

(58) Field of Classification Search
CPC ......... A61C 8/0089; A61C 1/07; A61C 1/084; A61B 17/1673
See application file for complete search history.

(56) References Cited

U.S. PATENT DOCUMENTS

| 6,716,030 | B1 | 4/2004 | Bulard et al. |
|---|---|---|---|
| 7,112,063 | B2 | 9/2006 | Bulard et al. |
| 8,043,089 | B2 | 10/2011 | Bulard et al. |
| 8,651,866 | B2 | 2/2014 | Bulard et al. |
| 2005/0037319 | A1 | 2/2005 | Bulard et al. |
| 2006/0269903 | A1 | 11/2006 | Bulard et al. |
| 2006/0275735 | A1 | 12/2006 | Bulard et al. |
| 2007/0015102 | A1 | 1/2007 | Vercellotti et al. |
| 2008/0241791 | A1 | 10/2008 | Bulard et al. |
| 2010/0105011 | A1* | 4/2010 | Karkar ............... A61C 13/0004 433/215 |
| 2010/0167235 | A1 | 7/2010 | Vercellotti et al. |
| 2010/0240009 | A1 | 9/2010 | Gogarnoiu |
| 2012/0034578 | A1 | 2/2012 | Bulard et al. |
| 2012/0094254 | A1* | 4/2012 | Uchitel ................ A61C 8/0018 433/173 |
| 2013/0017507 | A1 | 1/2013 | Moffson et al. |
| 2013/0045461 | A1* | 2/2013 | Misch .................. A61C 8/0019 433/173 |
| 2013/0101961 | A1 | 4/2013 | Bulard |
| 2015/0342618 | A1* | 12/2015 | Nguyen ............. A61B 17/1688 433/27 |

FOREIGN PATENT DOCUMENTS

EP    2 361 693 A3    1/2017

* cited by examiner

*Primary Examiner* — Nicholas D Lucchesi
(74) *Attorney, Agent, or Firm* — Norris McLaughlin, P.A.

(57) ABSTRACT

A method of placing a dental implant at an implant site in the jaw bone of a patient, said method comprising:
(a) without reflecting soft tissue covering the implant site causing a tip of a piezoelectric device to pierce the soft tissue so that the tip comes into direct contact with underlying jaw bone at the implant site;
(b) making a starter bore, but not a full-depth osteotomy, at the implant site with the piezoelectric device; and
(c) placing the dental implant into the implant site through the starter bore.

Alternatively, a tissue punch may be used to create a hole in the soft tissue through which hole access can be gained to the underlying jaw bone for subsequent starter boring with the piezoelectric device.

4 Claims, No Drawings

IMPLANTATION METHOD USING A PIEZOELECTRIC DEVICE

PRIORITY CLAIM

This application claims priority of U.S. Provisional Application Ser. No. 62/481,736, filed Apr. 5, 2017, the contents of which are hereby incorporated by reference.

BACKGROUND OF THE INVENTION

1. Field of the Invention

The present invention relates to a method of seating a dental implant into jawbone.

2. Description of Related Art

Piezoelectric devices are known for use in dentistry, including the preparation of holes in jaw bone for placing dental implants. See, for example, U.S. Patent Publications Nos. 2007/0015102; 2010/0167235; 2010/0240009; and 2013/0045461; the entire contents of which documents are incorporated herein by reference. The use of piezoelectric devices, which vibrate rather than rotate, for such purposes has a number of advantages compared to conventional drills, including: (a) greater precision; (b) reduction of heat produced during the cutting; (c) production of holes freer of bone debris; and (d) selective drilling of bone tissues (as the frequencies used for piezoelectric devices are ineffective for soft tissues).

The latter advantage can actually be a disadvantage at the start of the procedure as the inability of the piezoelectric device to impact soft tissue requires that the soft tissue covering jaw bone be reflected, i.e., cut or folded back to expose the underlying bone. See, for example, paragraph [0050] of U.S. Patent Publication No. 2007/0015102.

My prior patents and applications, which generally relate to placement of mini-implants, describe a placement protocol that involves making a starter hole in the patient's jawbone through the soft tissue without reflecting the soft tissue using a rotary drill directly through the soft tissue into the bone. (These prior patents and applications include U.S. Pat. Nos. 6,716,030; 7,112,063; 8,043,089; and 8,651,866; and U.S. Patent Publications Nos. 2005/0037319; 2006/0269903; 2006/0275735; 2008/0241791; 2012/0034578; and 2013/0101961; the entire contents of which patents and applications are incorporated herein by reference.) This procedure is problematic in that the soft tissue is rotated, torn, and carried into the bone. The resulting tissue debris can then be seeded into the bone and cause failure of the implant as a result of gingival tissues attempting to grow in the bone and forming granulation tissue. This granulation tissue left in the starter hole could cause the implant to fail.

Also, when inserting a dental implant, the most advantageous method for making a starter hole in the bone would one that built up the least amount of friction and therefore the least amount of heat. Currently, piezoelectric devices, when used, are not used to make starter holes, but, rather, full depth osteotomy holes, i.e., a hole having a depth corresponding to the seated length of the implant. See, for example, paragraph [0053] of U.S. Patent Publication No. 2007/0015102. Also, there remains the problem that the soft tissue covering the implant site still needs to be reflected.

Accordingly, there remains a need to provide a method of seating an implant that does not require reflection of the soft tissue covering the implant site, and which allows the use of piezoelectric devices and, therefore, also the realization of the advantages thereof.

SUMMARY OF THE INVENTION

I have discovered that the above-mentioned and other problems associated with implantation using both conventional rotating drills and piezoelectric devices can be simultaneously solved and the advantages of piezoelectric technology fully realized by the protocols described hereinbelow. Thus, the present invention relates in a first embodiment to a method of placing a dental implant at an implant site in the jaw bone of a patient, said method comprising:
  (a) without reflecting soft tissue covering the implant site, causing a tip of a piezoelectric device to pierce the soft tissue so that the tip comes into direct contact with underlying jaw bone at the implant site;
  (b) making a starter bore, but not a full-depth osteotomy, at the implant site with the piezoelectric device; and
  (c) placing the dental implant into the implant site through the starter bore.

Alternatively, the present invention relates in a second embodiment to a method of placing a dental implant at an implant site in the jaw bone of a patient, said method comprising:
  (a) without reflecting soft tissue covering the implant site, using a tissue punch to create a hole in gingival tissue covering the implant site to reveal underlying jaw bone at the implant site;
  (b) pushing a tip of a piezoelectric device into the hole so that the tip comes into direct contact with the underlying jaw bone at the implant site;
  (c) making a starter bore, but not a full-depth osteotomy, at the implant site with the piezoelectric device; and
  (d) placing the dental implant into the implant site through the starter bore.

DETAILED DESCRIPTION OF THE INVENTION

The technique described herein is applicable to all implants that can be seated with a starter bore in the manner described. In a preferred embodiment, the implant is a mini-implant as described in one of my previous patents or publications mentioned previously. I specifically contemplate every possible combination of each of such mini-implants utilized in the inventive method described herein.

An unexpected finding was that the piezoelectric device had something different happen when used as described herein. With the piezoelectric device there is no rotary cutting motion so the vibration does not cut the soft tissue and therefore does not carry it into the bone. According to the invention, the sharp point of the piezoelectric device is pushed through the soft tissue like a needle directly into the bone. With this method the mini-implant is placed directly into the bone through the soft tissue without elevating a flap of tissue, which is different than the conventional use of the piezoelectric device, as reflection of soft tissue covering the implant site is required since the piezoelectric device only removes bone and not soft tissue.

In the alternative embodiment, if a punch of soft tissue is removed from the gingival tissue and the piezoelectric device is pushed through the punched out tissue, the dimensions of the piezoelectric device will typically be such that as the underlying jawbone is removed the body of the piezoelectric device will be contacted by the slightly stretched walls of the gingival tissue hole created. An example would be using a 1.5 mm tissue punch and a 2 mm piezoelectric device and a 2 mm dental implant. Pushing the piezoelectric device through the 1.5 mm hole created by the tissue punch would stretch the walls of the gingival tissue hole created slightly to accommodate the 2 mm piezoelectric device diameter. As it turns, the piezoelectric device would be contacted by the stretched soft tissue, which is somewhat elastic in nature, yet would not affect the soft tissue. The result would be that when the implant is ultimately placed, the soft tissue would remain present in close proximity to and tight around the implant, which is desirable.

The following non-limiting exemplary protocol illustrates practice of the present invention with an illustrative inventive dental implant containing a ball-shaped head, a non-circular abutment and optionally a cog in the threaded-shaft, for the purposes of illustration only:

Example

1. Jaw Anatomy Evaluation

The clinician should palpate the labio-lingual or bucco-lingual width dimensions to estimate the optimal direction and angulation for exploratory piezoelectric device entry through crestal soft tissue then through the cortical bone layer and finally, four to five millimeters into the underlying medullary bone. Bone calipers may also be used to estimate actual bony width, once crestal soft tissue anesthesia is obtained. A point probe may also be used to advantage in estimating soft tissue depth and quality of the underlying bone.

2. Piezoelectric Device Specifications

A useful device is Woodpecker® brand US-II piezoelectric device available from Guilin Woodpecker Medical Instruments, Co., Guilin, Guangxi, China. This precision tool is carefully speed controlled by a foot rheostat.

3. Bore Technique

The required bore is really a micro-addition in comparison to larger scale drilling operations for conventional implants. The primary idea here is to ignore the concept of a precise osteotomy and think of the site procedure as comparable to developing a minimal "starter" hole. Light pressure is applied sufficient to push the tip of the piezoelectric device through the overlying gingiva into contact with the jaw bone beneath. The piezoelectric device is then used to create the minimal starter hole, while at the same time cleaning any tissue debris out of the starter hole created.

4. Placement of Dental Implants

The placement of a dental implant into this pilot opening through overlying attached gingiva on the ridge crest is facilitated using a small implant carrier device and then using the same device to initiate the self-tapping process by turning the carrier clockwise between thumb and index finger while exerting downward pressure on the abutment held in the long axis of the implant. This process provides the initial "take" into bone of the threaded portion of the implant body.

A winged thumb screw or analogous tool is used to continue the implant insertion process as soon as noticeable bony resistance is experienced and a more efficient tool is indicated. The wings of this device permit more thumb and finger purchase and control than the carrier tool. The thumb screw is kept in play until once again obvious resistance is encountered during the insertion process.

Ratchet and abutment head adapter tools are next utilized for the final stage of implant insertion, where carefully controlled, small incremental ratchet turns will provide efficient self-tapping in everything except the very densest of bone and assurance that the implant will demonstrate a rocklike integration with the bone that can then indeed be immediately loaded for functionality. For extremely dense bone sites experienced at deep levels it may be preferable not to try and force the insertion process, but rather to reverse the ratchet and back out the implant. It is then entirely possible to drill through the dense bone. The implant may then be reintroduced into the self-tapped site with carrier and thumb screw devices until once again resistance is met, at which point the ratchet and adapter are again employed to finalized the seating of the implant up to its abutment head protruding from the gingival soft tissue at its full length but with no neck or thread portions visible ideally.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A method of placing a dental implant at an implant site in the jaw bone of a patient, said method comprising:
   (a) without reflecting soft tissue covering the implant site causing a tip of a piezoelectric device to pierce the soft tissue so that the tip comes into direct contact with underlying jaw bone at the implant site;
   (b) making a starter bore, but not a full-depth osteotomy, at the implant site with the piezoelectric device; and
   (c) placing the dental implant into the implant site through the starter bore.

2. The method according to claim 1, wherein the dental implant is a mini-implant.

3. A method of placing a dental implant at an implant site in the jaw bone of a patient, said method comprising:
   (a) without reflecting soft tissue covering the implant site, using a tissue punch to create a hole in gingival tissue covering the implant site to reveal underlying jaw bone at the implant site;
   (b) pushing a tip of a piezoelectric device into the hole so that the tip comes into direct contact with the underlying jaw bone at the implant site;
   (c) making a starter bore, but not a full-depth osteotomy, at the implant site with the piezoelectric device; and
   (d) placing the dental implant into the implant site through the starter bore.

4. The method according to claim 3, wherein the dental implant is a mini-implant.

* * * * *